(12) United States Patent
Haldar et al.

(10) Patent No.: US 8,715,731 B2
(45) Date of Patent: May 6, 2014

(54) PROCESS OF REDUCING THE BITTER TASTE OF WATER SOLUBLE ACTIVES BY CO-GRINDING THE ACTIVE WITH β CYCLODEXTRIN

(75) Inventors: Rama Haldar, Randolph, NJ (US); Dipan Ray, Old Bridge, NJ (US); Deborah Tobia, Hillsborough, NJ (US); Donald Koelmel, Asbury, NJ (US); Sidney Etienne, Ridgefield Park, NJ (US)

(73) Assignee: ISP Investments Inc., Wilmington, DE (US)

( * ) Notice: Subject to any disclaimer, the term of this patent is extended or adjusted under 35 U.S.C. 154(b) by 1104 days.

(21) Appl. No.: 11/726,305

(22) Filed: Mar. 21, 2007

(65) Prior Publication Data

US 2007/0259931 A1 Nov. 8, 2007

Related U.S. Application Data

(60) Provisional application No. 60/784,742, filed on Mar. 22, 2006.

(51) Int. Cl.
*A61K 47/40* (2006.01)
*A61K 9/20* (2006.01)
*A61K 9/36* (2006.01)
*A61K 31/425* (2006.01)
*A61K 31/435* (2006.01)
*A61K 47/00* (2006.01)

(52) U.S. Cl.
USPC ........... 424/484; 424/464; 424/479; 514/277; 514/370; 514/772; 514/778

(58) Field of Classification Search
USPC .......... 424/464, 479, 484; 514/370, 772, 778, 514/277
See application file for complete search history.

(56) References Cited

U.S. PATENT DOCUMENTS

| 5,164,380 A * | 11/1992 | Carli et al. ...................... 514/58 |
| 5,476,654 A * | 12/1995 | Conte et al. ................. 424/78.08 |
| 6,444,703 B1 * | 9/2002 | Kamoda et al. ................ 514/553 |
| 2004/0115258 A1 * | 6/2004 | Stroppolo et al. ............ 424/465 |

OTHER PUBLICATIONS

Ahn, G. B. et al. , Preparation method of Chewable Tablet of Famotidine, Dec. 2004, KR 2004110376 A, Derwent Abstract, pp. 1-3.*

* cited by examiner

*Primary Examiner* — Sue Liu
*Assistant Examiner* — Andriae M Holt
(74) *Attorney, Agent, or Firm* — William J. Davis

(57) ABSTRACT

A process for reducing the intensity of the intrinsic bitter taste of a water soluble active which comprises dry mixing of said active with β-cyclodextrin.

7 Claims, No Drawings

PROCESS OF REDUCING THE BITTER TASTE OF WATER SOLUBLE ACTIVES BY CO-GRINDING THE ACTIVE WITH β CYCLODEXTRIN

This application claims priority of U.S. Provisional Application Ser. No. 60/784,742 filed Mar. 22, 2006, the disclosure of which is hereby incorporated by reference in its entirety.

BACKGROUND OF THE INVENTION

1. Field of the Invention

This invention relates to a process for reducing the bitter taste of water soluble actives, e.g. drugs, and, more particularly to a process of co-grinding such actives with beta-cyclodextrin to form an inclusion complex which masks the intrinsic bitter taste of such drugs.

2. Description of the Prior Art

Some water soluble actives may possess intrinsically bitter taste which makes them very unpleasant to take orally. Beta-cyclodextrin is known to mask this bitter taste when combined with the drug as an inclusion complex. See J. Szejtli et al, European J. of Pharmaceutics and Biopharmaceutics 61 (2005) 115-125 and references cited therein. However, complex formation is a slow process, particularly when the components are admixed in the solid state. Accordingly, it is desired to provide a new and improved process of preparing such inclusion complexes and of using such complexes to mask the bitter taste of the drug active.

SUMMARY OF THE INVENTION

A process for reducing the intensity of the intrinsic bitter taste of a water soluble active which comprises dry mixing of said active with β-cyclodextrin.

A process wherein said active is a drug.

A process wherein said inclusion complex comprises said active and said β-cyclodextrin in minimum of 1:1 molar ratio.

A process wherein said dry mixing step is carried out by co-grinding said active and said β-cyclodextrin.

A process wherein said co-grinding step is carried out in a ball mill.

A co-grinding process which is carried out for at least 1 hour at <30 rpm.

A process wherein said active is water soluble.

A process wherein the degree of formation of said inclusion complex upon dry mixing is at least 50% of said active and β-cyclodextrin.

A process wherein said active has a water solubility of at least 1 mg/ml.

The product of the process.

A tablet made from the product.

A process wherein said drug is doxilamine succinate or famotidine.

A process wherein the intensity of the bitter taste of said active is reduced by at least 50%.

DETAILED DESCRIPTION OF THE INVENTION

The invention will now be described in more detail with reference to the following working examples.

Example 1

A blend of 20 g of doxilamine succinate (active) having a water solubility of 1 g/ml and an intrinsic bitter taste, and 80 g of β-cyclodextrin (1:1 molar ratio) was subjected to co-grinding in a bal mill at a slow speed of 27 rpm for 1 hour. The degree of formation of an inclusion complex between the drug and β-cyclodextrin was determined quantitatively by Differential Scanning Calorimetry (DSC). The results are given in Table 1 below:

TABLE 1

| Drug Content (%) | ΔH (J/g) from DSC (pure drug) | ΔH (J/g) DSC (complex) | % Inclusion Complex |
|---|---|---|---|
| 20 | 122.9 | 15.0 | 50 |

The product was then evaluated by a taste panel for reduction of bitter taste intensity of the active in the form of inclusion complex. The average % reduction of bitter taste in the product was 50% as compared to the drug itself.

Example 2

A blend of 25 g famotidine (active) having a water solubility of 1 mg/ml and an intrinsic bitter taste, and 75 g of β-cyclodextrin (1:1 molar ratio) was subjected to co-grinding as in Example 1. The results are given in Table 2 below.

TABLE 2

| Drug Content (%) | ΔH (J/g) from DSC (pure drug) | ΔH (J/g) DSC (complex) | % Inclusion Complex |
|---|---|---|---|
| 25 | 168.9 | 10.5 | 70 |

The product was then evaluated by a taste panel for reduction of bitter taste intensity of the active present in the inclusion complex. The average % reduction of bitter taste in the product was 50% as compared to the drug itself.

What is claimed is:

1. A process for reducing the intensity of the intrinsic bitter taste of a water soluble active, the process comprising dry mixing of said active with β-cyclodextrin for at least one hour at <30 rpm to form an inclusion complex, wherein the degree of formation of said inclusion complex upon dry mixing is at least 50% of said active and β-cyclodextrin, as determined quantitatively by Differential Scanning calorimetry (DSC); wherein said dry mixing step is carried out by co-grinding said active and said β-cyclodextrin in a ball mill, and wherein said active is famotidine.

2. A process according to claim 1 wherein said inclusion complex comprises said active and said β-cyclodextrin in about a 1:1 molar ratio.

3. A process according to claim 1 wherein said active has a water solubility of at least 1 mg/mL.

4. The product made from a process for reducing the intensity of the intrinsic bitter taste of a water soluble active, the process comprising dry mixing of said active with β-cyclodextrin for at least one hour at <30 rpm to form an inclusion complex, wherein the degree of formation of said inclusion complex upon dry mixing is at least 50% of said active and β-cyclodextrin, as determined quantitatively by Differential Scanning Calorimetry (DSC); wherein said dry mixing step is carried out by co-grinding said active and said β-cyclodextrin in a ball mill, and wherein said active is famotidine.

5. A tablet made from the product of a process for reducing the intensity of the intrinsic bitter taste of a water soluble active, the process comprising dry mixing of said active with β-cyclodextrin for at least one hour at <30 rpm to form an inclusion complex, wherein the degree of formation of said inclusion complex upon dry mixing is at least 50% of said active and β-cyclodextrin, as determined quantitatively by Differential Scanning Calorimetry (DSC); wherein said dry mixing step is carried out by co-grinding said active and said β-cyclodextrin in a ball mill, and wherein said active is famotidine.

6. A process according to claim 1 wherein the intensity of the bitter taste of said active is reduced by at least 50%.

7. A process for reducing the intensity of the intrinsic bitter taste of doxilamine succinate, the process comprising dry mixing of the doxilamine succinate with β-cyclodextrin to form an inclusion complex.

* * * * *